(12) United States Patent
Drost et al.

(10) Patent No.: US 7,009,698 B2
(45) Date of Patent: Mar. 7, 2006

(54) INSPECTION SYSTEM AND METHOD

(75) Inventors: Jeffrey D. Drost, Flanders, NJ (US); Bruce A. Pellegrino, Far Hills, NJ (US)

(73) Assignee: Envirosight LLC, Randolph, NJ (US)

( * ) Notice: Subject to any disclaimer, the term of this patent is extended or adjusted under 35 U.S.C. 154(b) by 18 days.

(21) Appl. No.: 10/369,330

(22) Filed: Feb. 19, 2003

(65) Prior Publication Data
US 2004/0160600 A1 Aug. 19, 2004

Related U.S. Application Data

(63) Continuation of application No. 09/564,953, filed on May 4, 2000, now Pat. No. 6,538,732.

(60) Provisional application No. 60/132,400, filed on May 4, 1999.

(51) Int. Cl.
*G01N 21/00* (2006.01)
*G03B 17/00* (2006.01)

(52) U.S. Cl. .................... 356/241.1; 352/243

(58) Field of Classification Search .. 356/241.1–241.5; 358/87, 229, 224, 335, 199, 906, 288, 248; 352/243, 293; 248/168, 187, 188.6
See application file for complete search history.

(56) References Cited

U.S. PATENT DOCUMENTS

| | | | | |
|---|---|---|---|---|
| 5,065,249 A | * | 11/1991 | Horn et al. | 348/376 |
| 5,070,401 A | * | 12/1991 | Salvati et al. | 348/141 |
| 5,115,136 A | * | 5/1992 | Tomasch | 250/461.1 |
| 5,134,471 A | | 7/1992 | Gendron et al. | 358/100 |
| 5,193,405 A | * | 3/1993 | Oomichi et al. | 73/865.8 |
| 5,205,174 A | * | 4/1993 | Silverman et al. | 73/623 |
| 5,712,677 A | | 1/1998 | Fraering, Jr. et al. | 348/84 |
| 6,538,732 B1 | * | 3/2003 | Drost et al. | 356/241.1 |

FOREIGN PATENT DOCUMENTS

| | | |
|---|---|---|
| EP | 1051037 A2 * | 8/2000 |
| EP | 1 051 037 A2 | 11/2000 |
| FR | 2 705 152 A | 11/1994 |

OTHER PUBLICATIONS

Search Report dated Jul. 11, 2001, from the European Patent Office issued in the counterpart Application No. EP 00 10 9509.

* cited by examiner

*Primary Examiner*—Michael P. Stafira
(74) *Attorney, Agent, or Firm*—Synnestvedt & Lechner LLP (57) ABSTRACT

A process for maintaining an area using a non-invasive inspection device, the inspection device comprising at least: an imaging system having an adjustable field of view and an imaging device for transmitting an electrical signal corresponding to an area within the field of view; a portable support system operatively connected to the imaging system and adapted to provide functional support to the imaging system; and a positioning system connected to the imaging system and adapted for moving the imaging system independently of the portable support system; the process comprising: (a) positioning the imaging system independently of the support system such that a target area is in the field of view while at a first magnification level; (b) imaging a the target area at a second magnification level greater than the first magnification level; (c) outputting an image of the target area; (d) evaluating the image to determine whether the target area is acceptable or whether an invasive procedure needs to be performed; and (e) performing the invasive procedure on the target area if needed.

10 Claims, 11 Drawing Sheets

INSPECTION SYSTEM AND METHOD

REFERENCE TO RELATED APPLICATIONS

This application claims priority to provisional application No. 60/132,400, filed May 4, 1999, and is a continuation of U.S. application Ser. No. 09/564,953 now U.S. Pat. No. 6,538,732, filed on May 4, 2000. Both of these applications are hereby incorporated by reference.

FIELD OF INVENTION

The present invention relates generally to the inspection of areas which are hard-to-read, inaccessible or uninhabitable for humans. More specifically, the invention relates to the inspection of manholes and the lateral pipes radiating therefrom prior to invasive procedures such as cleaning and comprehensive exploratory inspections.

BACKGROUND OF THE INVENTION

It is often necessary to inspect and maintain areas under conditions which render them inaccessible or otherwise uninhabitable by humans for an extended period. These conditions include, for example, small confined spaces and harsh environments such as insufficient air/oxygen, presence of toxins, radioactivity, contamination, excessive dust, dirt and filth, and high noise levels. These conditions can be found in areas common to storm and sewer pipes, nuclear reactors and containments, fossil fuel plants and petrochemical refining facilities just to name a few. Although these present their own problems and complexities with respect to inspecting and maintaining, the inconvenient and time-consuming nature of performing the initial inspection is common to all.

For illustrative purposes the inspection of storm and sewer pipes is considered in detail, although the scope of the present invention is by no means limited to this application. Most municipalities contain a vast network of storm and sewer pipes which often represent the oldest infrastructure in the community. Periodically, these pipes must be inspected for problems such as cracks, blockage, build-up, and root infiltration. To this end, it is common for an invasive device such as a pipe crawler or push camera to be introduced into the pipe to perform the inspection.

Although effective in obtaining detailed images, using a pipe crawler is inconvenient and requires a great deal of time to set up and operate even if no problem is discovered. In other words, the pipe crawler is deployed regardless of whether a problem exists. Furthermore, the use of pipe crawlers is frequently limited by the size and configuration of pipes to be entered.

The inefficiencies associated with routine inspections are exacerbated in situations where the pipes need to be cleaned since pipe inspection and cleaning are typically performed by different personnel, often at different times. In a typical cleaning operation, an invasive inspection is performed initially to determine whether the pipes are blocked. Such an inspection tends to be excessive since blockage conditions can be determined usually without the precision required for assessing cracks and other pipe damage. If a blockage is detected, then cleaning personnel must be brought in to perform an invasive cleaning operation. Once the cleaning procedure is performed, a second inspection is typically required to ensure that the blockage has been removed. This second inspection requires the inspection personnel to return and perform yet another invasive inspection (which as mentioned above is excessive in the first instance) to confirm whether the blockage has been removed. If the cleaning was not sufficient, then the cleaning personnel must return to continue the cleaning operation, and the cleaning/inspection process is repeated yet again. Thus, in this cleaning process, an inconvenient and excessive inspection is repeated between each cleaning causing delays and driving up costs.

Therefore, there is a need for a more convenient approach to inspect and maintain underground pipes without the time and complexity associated with invasive techniques such as the use of pipe crawlers or push cameras. The present invention fulfills this need among others.

SUMMARY OF INVENTION

The present invention provides for a quick and convenient non-invasive approach to ascertain the condition of an inaccessible or uninhabitable area before initiating an invasive procedure such as a comprehensive inspection or cleaning. More specifically, rather than physically entering the area with a robotic or push camera, a highly-maneuverable, hand-held inspection system is provided which can be readily positioned to capture the area within its field of view, and then operated to zoom in on the area and obtain an image with the desired degree of detail. Thus, the device obtains images of inaccessible or uninhabitable areas by maneuvering an imaging device and using its magnification capabilities rather than by physically entering the area.

Once the images are obtained, an analysis may be performed to determine whether problems such as cracks, blockage, and root infiltration exist. The images obtained preferably are in a readily-transmitted form, such as a bitmap, thereby allowing them to be transmitted off-site for analysis if desired. If no problem is detected, then the device can be moved quickly to another area to perform another inspection. This way, the time of setting up and operating a pipe crawler or similar device is not wasted on areas that are in acceptable condition.

On the other hand, if a problem is detected, an invasive procedure may be performed to correct or further assess the problem. For example, if a crack is detected, a more comprehensive inspection may be performed in which an invasive inspection device, such as a pipe crawler or push camera, is introduced in the pipe to obtain detailed images pursuant to formulating a plan to remedy the situation. Likewise, if the initial inspection detects that a pipe is clogged, it may be cleaned contemporaneously by introducing an invasive cleaning device into the pipe to remove the obstruction. Thus, rather than awkwardly halting cleaning operations between invasive inspections, a blockage situation may be quickly and easily ascertained on the spot, preferably while the cleaning personnel standby.

To facilitate the inspection approach described above, several attributes of an inspection system have been identified. First, the device should be capable of performing an inspection both close up and from a distance, and, thus, it should have a relatively-high magnification ratio and a tolerance to low-light conditions. Second, the inspection system should be self-contained so as not to be encumbered with power cords or control leads. To this end, its power supply, operator's control, and monitoring/recording should be portable, preferably, carried on the user performing the inspection, or, alternatively, located on a mobile vehicle (such as a cleaning vehicle) which is proximate to the area being inspected. Third, the device should be highly maneuverable to position it such that the subject matter is in its field of view. Properties that add to maneuverability include, for example, light weight, conveniently situated controls, and means for positioning the imaging portion of the device. An extended boom, for example, allows the device to be inserted into difficult-to-reach areas. Fourth, the images obtained should be readily available for review and analysis to determine whether an invasive procedure is warranted. Preferably, a digital framegrabber is used to transform the image into a readily-transmitted medium, which, for example, can be transmitted via e-mail anywhere in the world for off-site analysis. Fifth, the device should be durable to withstand harsh environments and rugged use. The preferred device thus has no external wiring and is sealed to render it waterproof.

Accordingly, one aspect of the invention is a system having one or more of the above-referenced attributes for performing an inspection as described above. In a preferred embodiment, the system comprises: (a) an imaging system having an imaging device for transmitting an electrical signal corresponding to an area being imaged, and magnification functionality adapted to magnify the imaged area; (b) a portable support system for providing functional support to the imaging system, a controller for controlling the magnification functionality of the imaging device, and an image output device for outputting the image based on the electrical signal; (c) a positioning system connected to the imaging system and adapted for moving the imaging system independently of the support system.

Another aspect of the invention is a method of using the non-invasive inspection system for maintaining an area. In a preferred embodiment, the method comprises: (a) positioning the imaging system independently of the support system such that a target area is in the field of view while at a first magnification level; (b) imaging the target area at a second magnification level greater than the first magnification level; (c) outputting an image of the target area; (d) evaluating the image to determine whether the target area is acceptable or wether an invasive procedure needs to be performed; and (e) performing the invasive procedure on the target area if needed.

The method of the present invention is particularly applicable to inspecting and cleaning sewer and storm pipes which are accessible through a manhole. In a preferred embodiment, the method of inspecting and cleaning storm and sewer comprises: (a) extending an imaging system into a manhole; (b) imaging the interior of the manhole at a first magnification level; (c) locating a lateral pipe connected to the manhole; (d) imaging the interior of the lateral pipe at a second magnification level greater than the first level; (e) evaluating the image of step (d) to determine whether the lateral pipe is acceptable or whether an invasive procedure needs to be performed; and (f) preforming the invasive procedure on the lateral pipe if needed. Preferably, the invasive procedure is a cleaning procedure in which a cleaning tool invades the lateral pipe.

Yet another aspect of the invention is a method of inspecting using the non-invasive inspection device of the present invention while storing the image information in a database. In a preferred embodiment, the method comprises: (a) positioning the imaging system independently of the support system such that a target area is in the field of view while at a first magnification level; (b) imaging the target area at a second magnification level greater than the first magnification level; (c) outputting an image of the target area as a digital signal; and (d) storing the digital signal in a database. Preferably, the database comprises data corresponding to the location of the target area.

DETAILED DESCRIPTION OF PREFERRED EMBODIMENT

Figure 1:
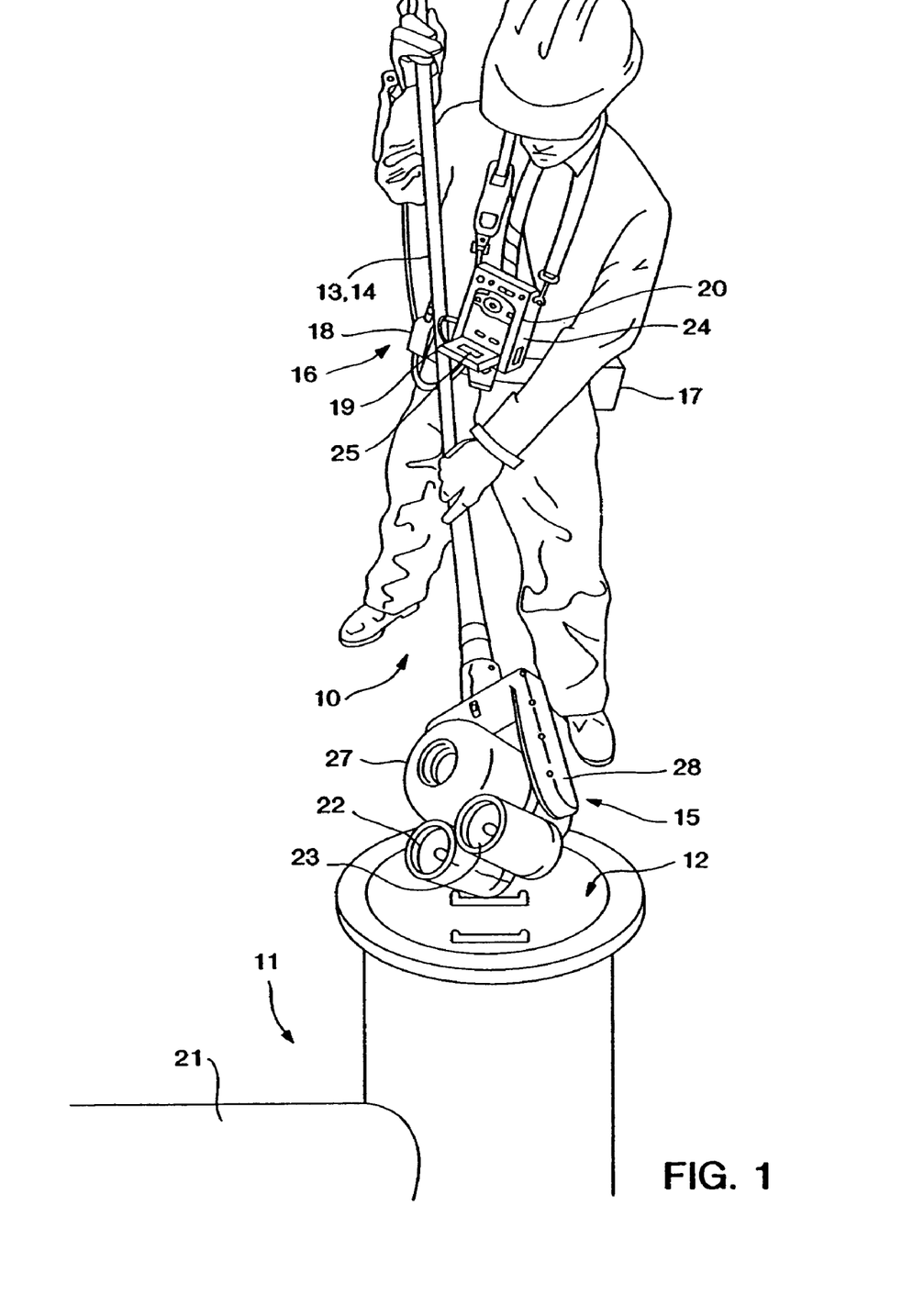
FIG. 1 shows a user inserting a preferred embodiment of the device into a manhole.

Referring to the drawings, FIG. 1 shows a user using a preferred embodiment of the inspection system 10 to ascertain whether an invasive procedure is warranted. Using the system comprises the steps of (a) positioning an imaging system 15 independently of a support system 16 such that a target area is in the field of view while at a first magnification level; (b) imaging a target area at a second magnification level greater than the first magnification level; (c) outputting an image of the target area; (d) evaluating the image to determine whether the target area is acceptable or whether an invasive procedure is warranted, and (e) performing the invasive procedure if necessary. Each of these steps is considered in greater detail below. It should be understood, however, that the classification of the process in these discrete steps is for illustrative purposes and should not be construed to limit the scope of the invention. For example, it is anticipated that two or more steps may be performed in a single operation or one or more steps may not be performed at all.

With respect to step (a), the user lowers the imaging system 15 into a manhole 12 using a positioning system 13 while observing a monitor 25. The positioning system 13 in this embodiment is a telescoping boom 14. The user is wearing a support system 16 for supporting the functionality of the imaging system 201. In this embodiment, the support system 16 comprises a power supply 17 and control functionality 18 worn on a belt 19, and monitoring and recording functionality 20 worn around the user's neck.

In step (b), the interior of the manhole is imaged initially. Imaging the interior of the manhole typically is performed in close proximity thereto and thus at a low magnification level which provides a wide field of view. The user then would inspect the manhole's condition and attempt to locate the penetration of a lateral pipe 21 in the manhole 12. It may be preferable to illuminate the interior of the manhole using a flood light 22 which provides a wash of light commensurate with the wide field of view. Once the entrance to the lateral pipe 21 is located, the user positions the imaging system 15 with the interior of the lateral pipe 21 in its field of view.

In step (c), the user increases the magnification level via the control functionality 18 to obtain images further down the pipe. It may be preferable to illuminate the viewed area using a spot light 23 which provides a high intensity, relatively-focused light commensurate with the relatively narrow field of view associated with high-magnification.

In step (d), images of the interior of the lateral pipe may be recorded and stored on a computer readable medium. In this embodiment, a digital image is recorded with a framegrabber 24 and stored on a disk (not shown). It may be preferable to store the digital information in a database along with data corresponding to the location of the imaged area. This location data may be, for example, a manhole number or designation, a street address, global coordinates, or map coordinates. In one preferred embodiment, the inspection system generates global coordinates using an onboard global position system (GPS). These coordinates are then stored along with the image in a database such that, when a particular imaged is viewed, its corresponding location is also displayed. It may be preferable to display the imaged area's location in the form of a reference point on a map. Displaying an object's position on a map using GPS coordinates is well known and systems for doing so are commercially available though such companies as TENET Defence Ltd., United Kingdom. In one particularly preferred embodiment, the image of the area is displayed on the region of a spot of a map corresponding to the area's location.

Once the images are obtained, they may be analyzed on-site or off-site to determine whether an invasive procedure is required. In the latter situation, it may be preferable to transmit a digital signal of the image over a telecommunicative link (e.g., the internet) to the off-site location. Accordingly, the preferred embodiment of the present invention enables a user to obtain quickly and conveniently digital images of lateral pipes for evaluation before invasive procedures are used.

In step (e), an invasive procedure may be undertaken to resolve the problem or further assess it. For example, if a crack is detected, a more comprehensive inspection may be performed in which an invasive inspection device, such as a pipe crawler or push camera, is introduced in the pipe to obtain detailed images pursuant to formulating a plan to remedy the situation. Likewise, if the initial inspection detects that a pipe is clogged, it may be cleaned contemporaneously by introducing an invasive cleaning device into the pipe to remove the obstruction. Given the convenience of the inspection system of the present invention, it is preferred that pipe cleaning procedures be modified to include follow-up inspections immediately after cleaning rather than calling in a specialized inspection team. In this respect, it may be preferable to physically integrate the inspection system with the cleaning system.

Figure 10:
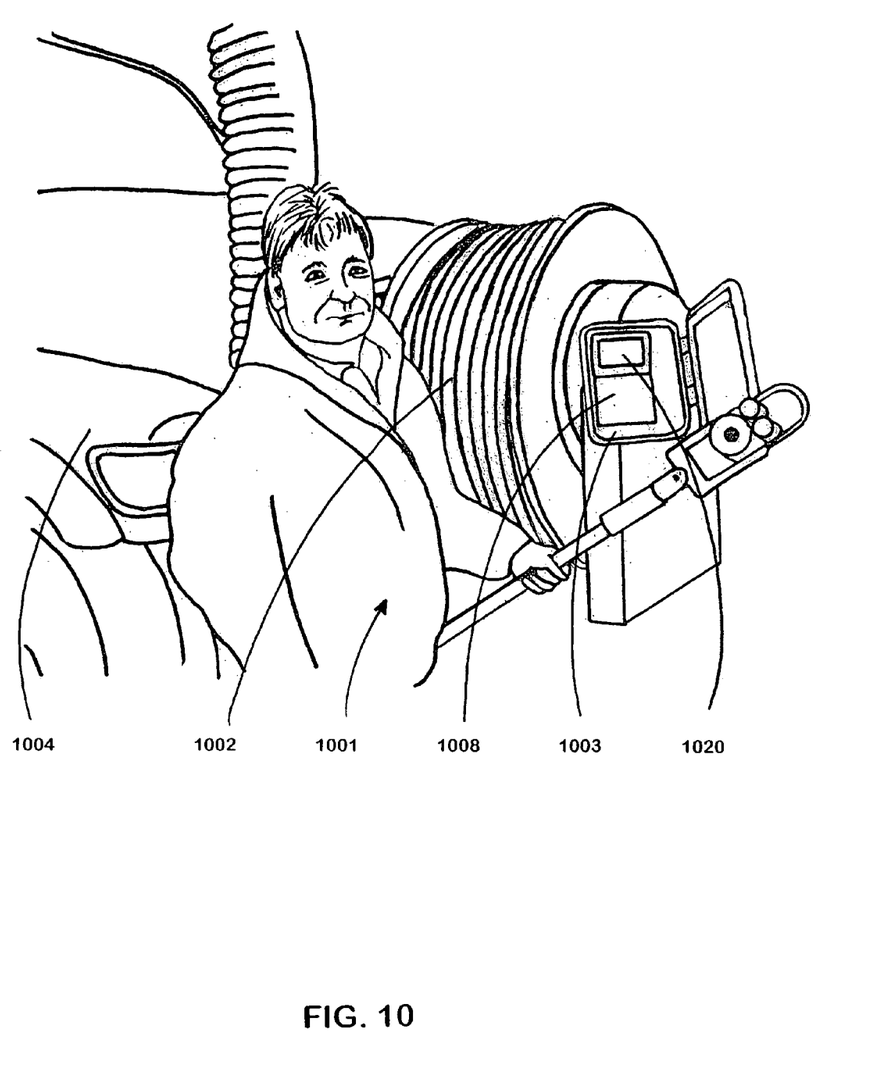
FIG. 10 shows the inspection system integrated with a vehicle used for cleaning storm and sewer pipes.

In FIG. 10, the inspection system 1001 of the present invention is shown integrated with a truck-mounted pipe cleaning system 1002. Specifically, the support system 1003 of the inspection system is integrated with a storm and sewer pipe cleaning system 1002 on a truck 1004. In particular, the power supply (not shown) of the truck 1004 is used to power the inspection system. This is advantageous as the user is no longer encumbered with heavy batteries and the like. Additionally, the operator control functionality 1008 and monitoring and recording functionality 1020 is also mounted to the truck, thereby lightening the load the user must carry. (As shown in FIG. 1, in one preferred embodiment, the operator control functionality is worn by the user on a belt and the monitoring and recording functionality is supported by a strap around the user's neck.) Therefore, by integrating pipe cleaning and inspection of pipes, synergies can be realized not only in performing the procedures, but also in the equipment used to perform the procedures.

Although FIG. 1 depicts the inspection of a pipe through a manhole, it should be understood that the present invention is applicable to the inspection of any area located in an inaccessible and/or uninhabitable location as described above. For example, the device may be used to quickly and conveniently inspect the containment of a nuclear reactor without erecting scaffolding. By performing inspections quickly without extensive set-ups, the overall radiation dose incurred by personnel is reduced. Additionally, in addition to nuclear reactors, the inspection system of the present invention can be used in a host of other applications including, for example, the inspection of snubbers, pipe hangers, pipe insulation, storage vessels, and the like which are commonly found in power generating stations (such as fossil fuel, nuclear, and hydro), refineries, and, practically speaking, any other significant industrial facility. Furthermore, aside from industrial applications, the system of the present invention may be used for examining vehicles or structures for evidence of terroristic activity. For example, rather than crawling under a truck or enter a confined space that might contain a bomb or biological threat, the inspection system may be used first to determine whether a closer inspection or perhaps robotic intervention (e.g., bomb defusing) is required.

Figure 2:
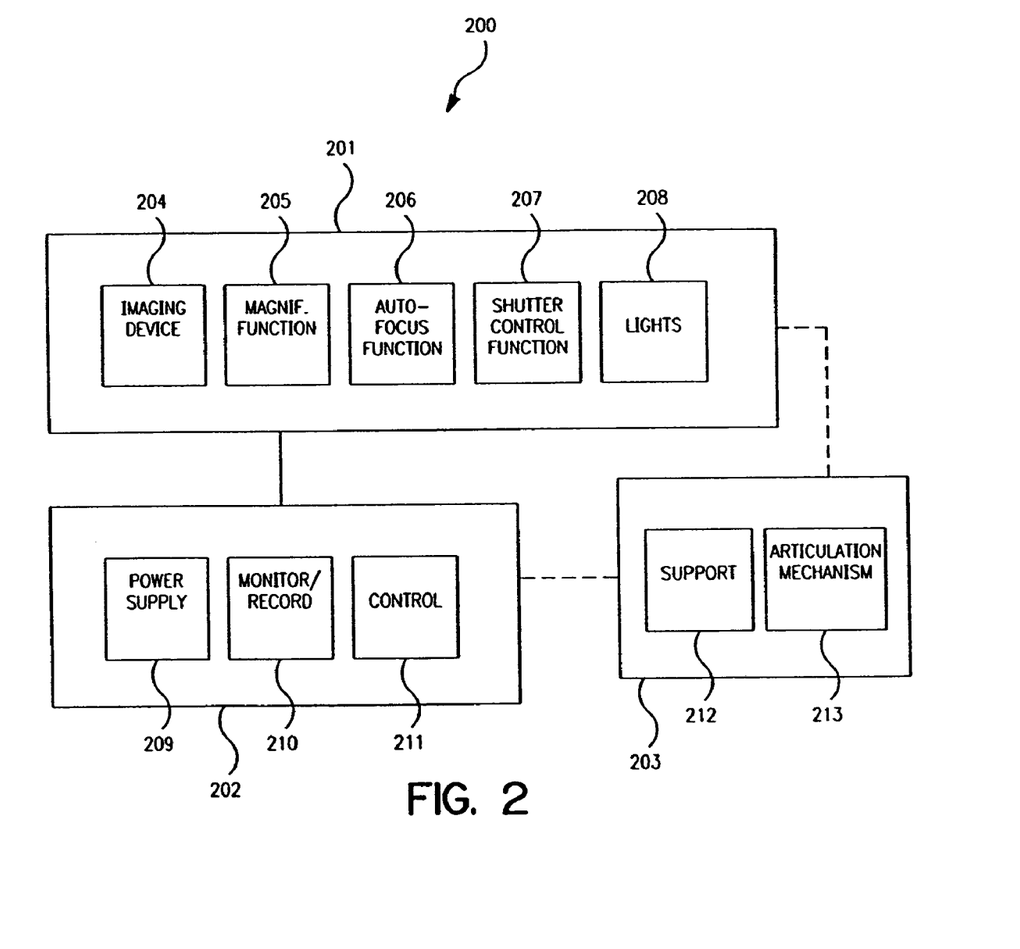
FIG. 2 shows a schematic of the system.

Now referring to FIG. 2, the subsystems of the inspection system will be described in greater detail. For illustrative purposes, the system 200 may be divided into the following subsystems: (1) the imaging system 201, (2) the support system 202 for supporting the functionality of the imaging system 201, (3) the positioning system 203 for physically positioning the imaging system 201, and, optionally, (4) a GPS system 215 for providing location data on the imaging system 201 and (5) a measuring system 214 for providing dimensional information of the images generated by the imaging system 201. It should be understood that the division of the system into various components is for illustrative purposes and should not be construed to limit the scope of the invention. Indeed, the various systems may be further divided into subsystems, or their various components and functions may be combined and integrated.

1. Imaging System 201

The function of the imaging system is to generate and transmit an electrical signal corresponding to an area being imaged. The heart of the imaging system is an imaging device 204 which translates an image to an electrical signal. The imaging device 204 may be any conventional or subsequently-developed device for imaging a target object. The term "imaging" broadly refers to a characterization or representation of the target object based on a particular property, such as, for example, its tendency to reflect or absorb electromagnetic radiation, its thermal profile, or its acoustical profile. Devices for imaging these characteristics or properties are known and include, for example, video cameras, still cameras, digital cameras, infrared detectors, X-ray machines, lasers, microphones, sonic or ultrasonic transducers, radar, and the like.

In the preferred embodiment, the imaging device 204 provides a video image of the target area. More preferable, the imaging device comprises a charge coupled device (CCD) which is well known in the art. The CCD electronically captures an image of the video field in an analog format and the analog information is relayed to the monitor/digital recording functionality 210 of the support system 202.

Preferably, the CCD is a low lux CCD having a sensitivity of at least 6 Lux at f1.4, and, more preferable at least 3 Lux at f1.4.

The imaging system 202 also includes a lens/magnification system 205 having inherent optical characteristics such as distortion, focal length, and field of view, some of which are used in the calculation of the target size as is described in detail below. The preferred optical characteristics of the imaging system include a focal length of about 4 mm to about 74 mm, a field of view of about 2.7° to about 48°, and a minimum focal distance of about 10 mm to about 800 mm. The lens/magnification system comprises a series of lenses that interact to change the focus and magnification. As is known in the art, the system includes motors that manipulate the positioning of the various individual lenses in relation to each other and in relation to the CCD in order to effect different foci and magnification configurations.

The lens/magnification system 205 should contain magnification functionality with a relatively high magnification ratio. More specifically, the intended applications of the inspection system of the present invention usually require a panoramic, wide angle view for general viewing, and a magnified view for details. Again, such functionality is well known in the art and may comprise, for example, optical magnification or electronic magnification using techniques such as pixel enlargement or interpolation. In a preferred embodiment, the magnification has a magnification ratio of no less than about 6:1, more preferably, no less than about 12:1, and even more preferable, no less than about 50:1. In a highly preferred embodiment, the magnification ratio is 72:1 and is the composite of an 18:1 optical zoom and a 4:1 digital zoom.

The imaging system preferably comprises autofocus functionality 206. Again, autofocusing is known in the art. More preferably, the imaging system provides for manual focusing thereby allowing the user to control the focus if, for example, the autofocus is focusing on the wrong object.

In a preferred embodiment, the imaging system also enables the user to control the shutter speed manually through shutter control functionality 207. More specifically, in certain applications, for example, in low light conditions, it may be desirable for the user to extend the exposure time to increase the amount of light in the image. For example, shutter speed may be increased from a typical period of about 1/60 second to about 1/3 second.

Suitable imaging system having the above-mentioned magnification and functionality are commercially available from, for example, Sony Company (Model No. FCB-IX47).

In the preferred embodiment, the imaging device and the above-mentioned functionality are integrally packaged. Furthermore, this package may be enclosed within an enclosure, as discrete units, or its structure may be integral to the enclosure. Preferably, the enclosure is splash proof. More preferable, the enclosure is sealed and watertight thereby allowing it to be submerged. To this end, it may be desirable to pressurize the enclosure to match the anticipated hydrostatic pressure to minimize the risk of leakage.

In a preferred embodiment, the imaging system comprises one or more lights 208 to illuminate the target area and improve the quality of the images obtained. Given the relatively high magnification ratios of the imaging system, it is preferable to provide at least two types of lights, a flood light and a spot light. The function of these lights is well known in the art. Specifically, a flood light is useful for illuminating a relatively close, broad area, while a spot light illuminates a focused area at a further distance. The lights may be packaged individually or in combination, and may be integral with the imaging device or separate therefrom.

2. Support System 202

The support system 202 is a portable system and functions to support the functionality of the imaging system 201. Supporting the functionality of the imaging system requires providing the imaging system with power and control. To this end, a preferred support system comprises a power supply 209, operator's control 211, and monitoring/recording functionality 210.

Figure 1A:
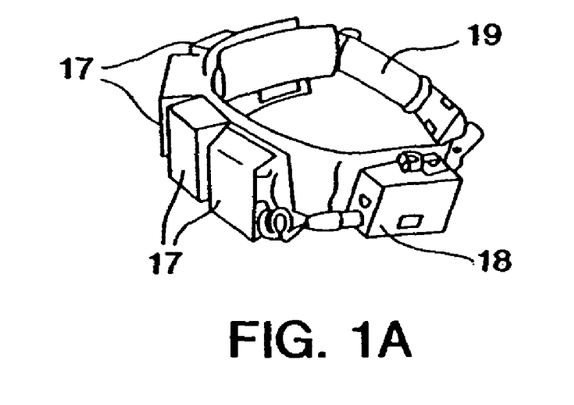
FIG. 1a shows the belt of the preferred embodiment of FIG. 1.

In a preferred embodiment, the power supply and operator's control are mounted on a belt 19 as shown in FIG. 1a adapted to be worn by the user. The power supply 209 supplies power to the imaging system and to other components of the support system requiring power. Preferably, the power is supplied by one or more rechargeable batteries releasably mounted to the belt 19 as shown in FIG. 1. Given the weight of batteries, particularly wet cells, it may be preferable under some circumstances to place one or more batteries on the ground during operation of the inspection system. Although rechargeable belt-mounted batteries are preferred, power may be provided through other conventional means such as a portable generator.

The operator's control 18 is used to control the on/off operation of the imaging device as well as the other functions such as magnification, manual focus and shutter speed. In a preferred embodiment, this control functionality is integrated into a single enclosure as shown in FIG. 3a–e. This figure shows five sides of a housing which is adapted to be mounted to the belt 19 as shown in FIG. 1a.

Figure 3A:
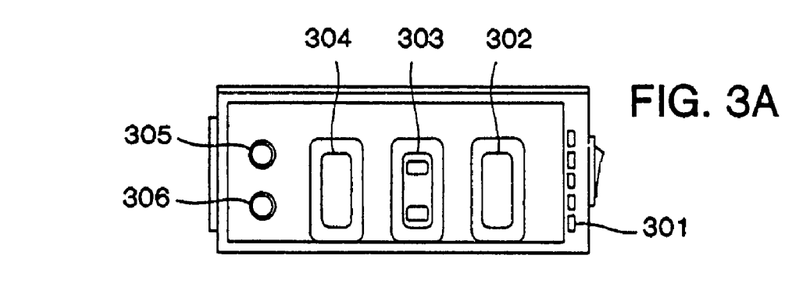
FIGS. 3a–e show the operator's control in the preferred embodiment of FIG. 1.

FIG. 3a is a top view of the housing and shows the following controls: a series of LEDs 301 which are used to provide an indication of battery life; a momentary-on rocker switch 302 for adjusting the magnification from wide angle to telescopic; a three-position rocker switch 303 with LEDs indicator lights for light control such that when one side is depressed the flood light is on, when the other side is depressed the spot light is on, and when in the middle, both lights are off; a momentary-on rocker switch 304 the operator uses to send signals to the focus and zoom motors in order to change the positioning of the lenses in the lens/magnification 205 for optimum viewing. Preferably, the focus and zoom motors contain servo-feedback mechanisms which provide information to a microprocessor (discussed below); a manual/autofocus selector knob 305 with an LED indicator; and a shutter speed control knob 306 with an LED indicator.

Figure 3B:
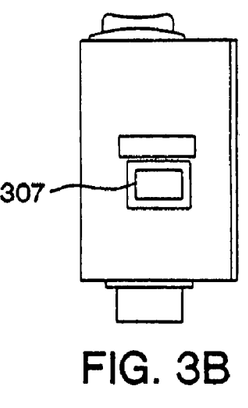
Figure 3C:
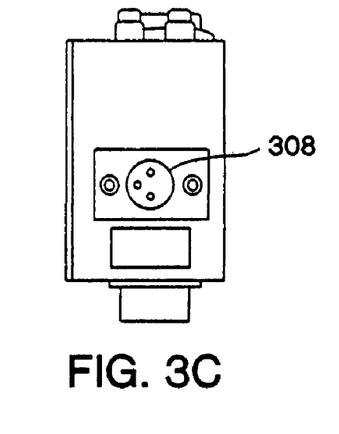
Figure 3D:
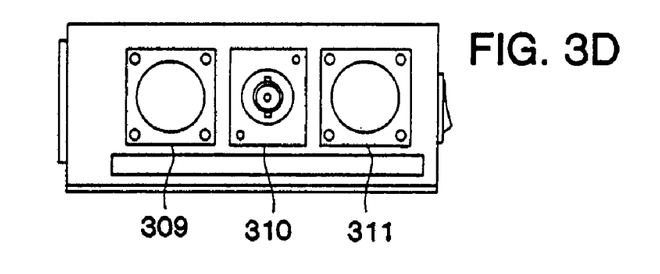
Figure 3E:
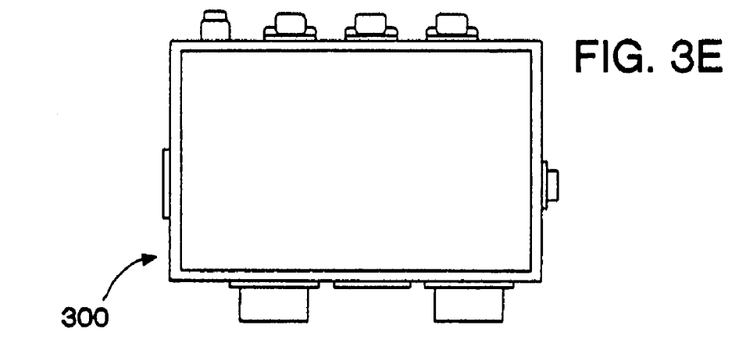

FIG. 3b is a side view of the control housing and shows a main on/off switch 307 for turning the imaging system on and off. FIG. 3c is the other side view and shows the power input 308 to supply power to the various control functionality. FIG. 3d is a bottom view of the control housing and shows: an input 309 for the video signal from the imaging system; a video output 310 to the monitor/framegrabber (described below); and an optional output 311 for remote monitoring or recording.

Figure 4:
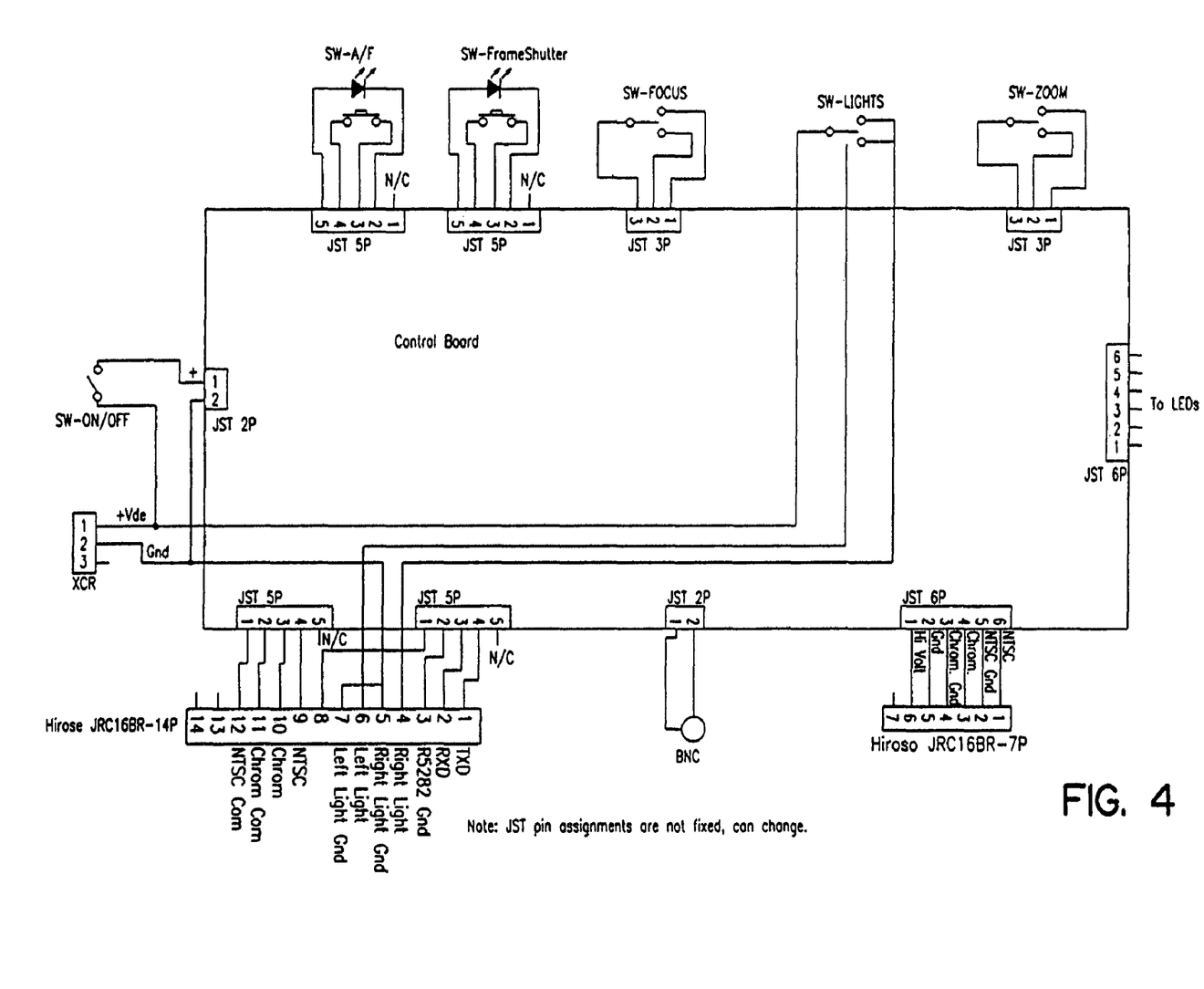
FIG. 4 shows a layout diagram of the circuit board of the operator's control of FIG. 3.
Figure 5A:
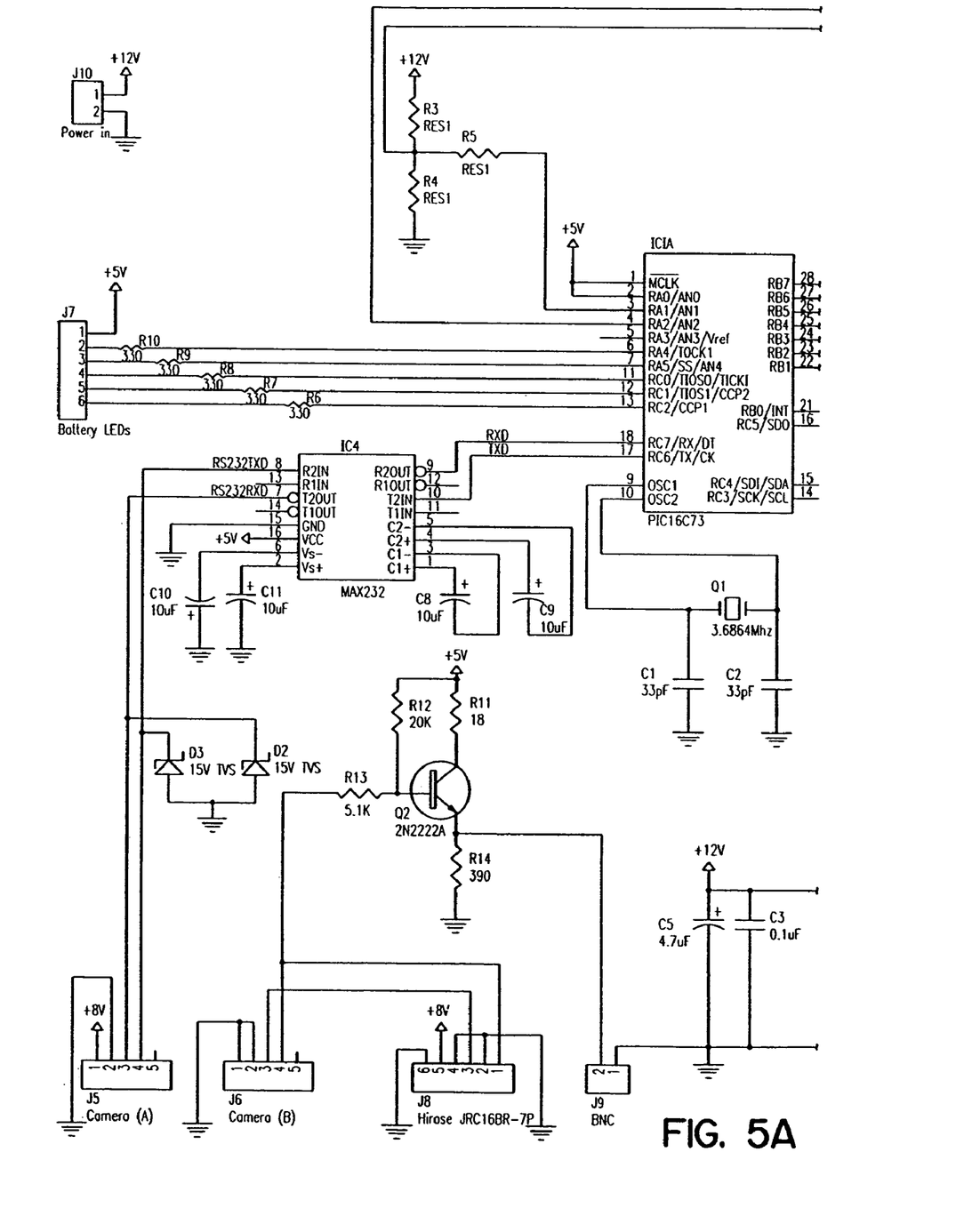
FIG. 5 shows a detailed schematic diagram of the circuit board of FIG. 4.
Figure 5B:
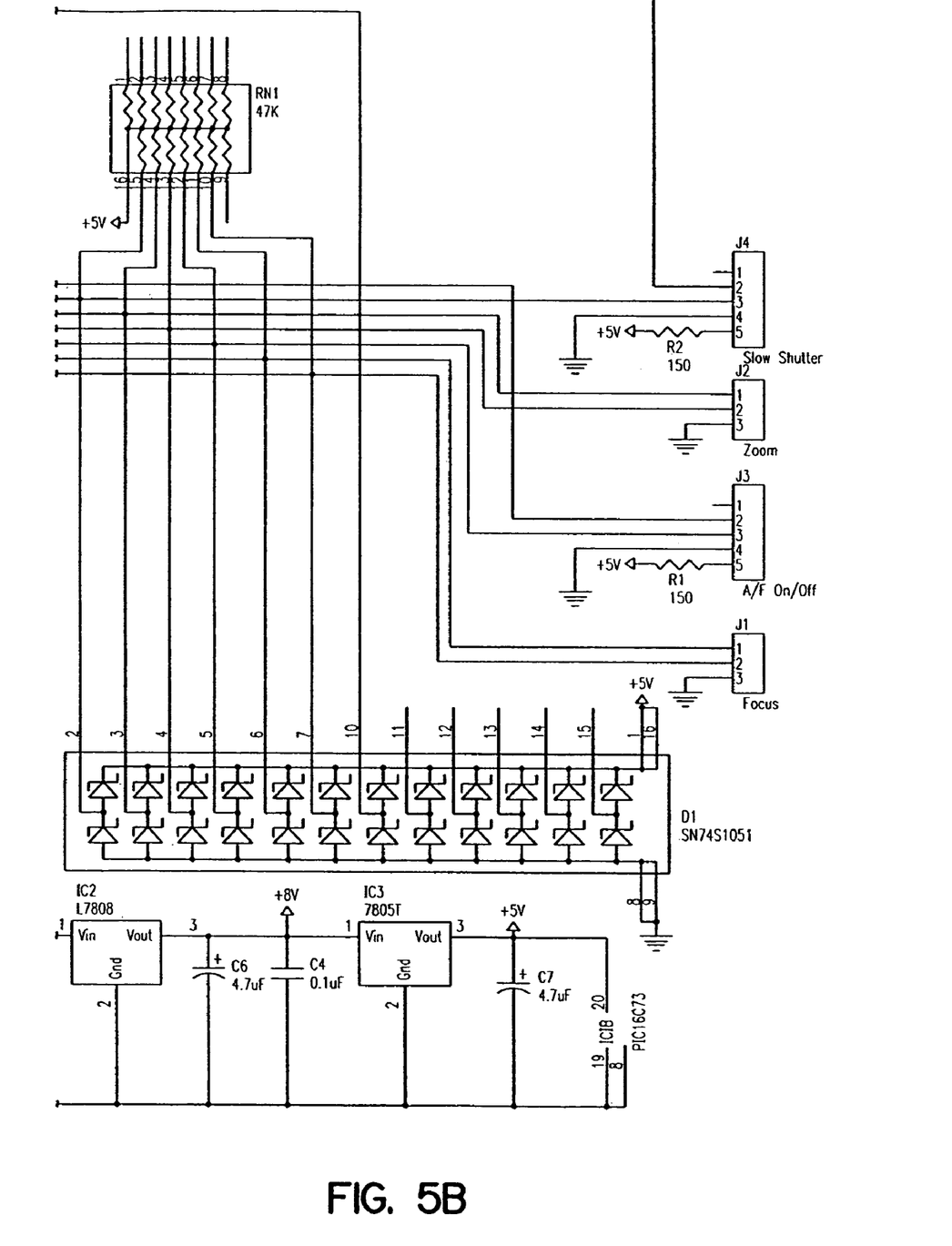

FIG. 4 shows a layout diagram of a preferred embodiment of a circuit board housed within the control housing of FIGS. 3a–e. As shown, the circuit board interfaces the various control functionality and transmits commands to and receives acknowledgments from the imaging system. In a preferred embodiment, the circuit board comprises a programmable controller (IC1A) as shown in the circuit board's schematic in FIG. 5. The programmable controller provides for a configurable control functionality where the function of the switches described above may be reconfigured through a simple software change. Although the control functionality may be hardwired directly to the imaging system, interfacing the imaging system through a circuit board having a programmable controller is preferred from a flexibility standpoint. Additionally, the communication link between the control functionality and the imaging system may be metallic or wireless, although metallic is preferred.

Figure 1B:
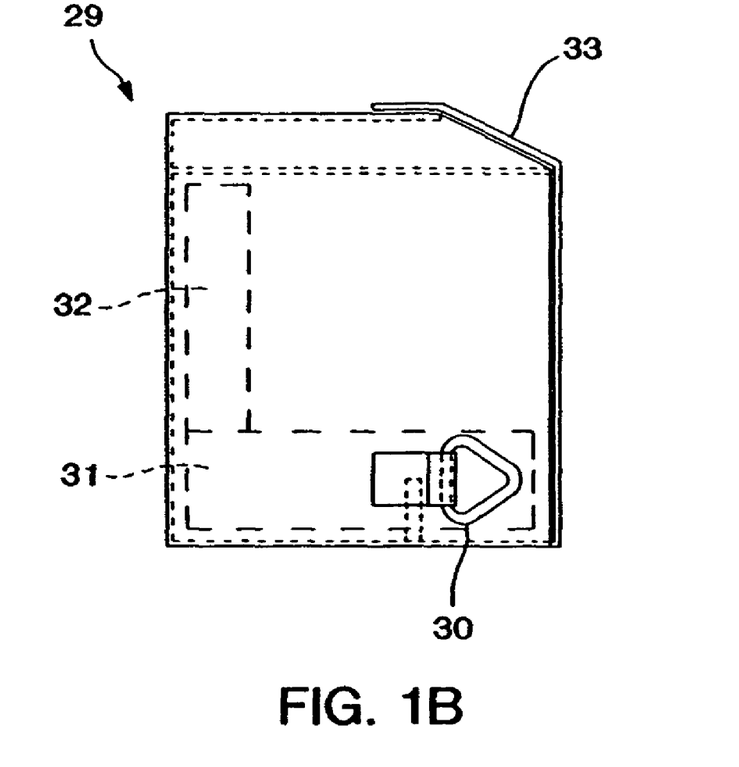
FIG. 1b shows a bag for supporting the monitor/recording device of FIG. 1.

Referring back to FIG. 2, the output device 210 preferably comprises a monitor which allows the user to view the images being transmitted by the imaging system in real time. Such a function is highly preferred as it provides feedback to the user as he or she positions the imaging system. Monitoring devices are well known in the art. In the preferred embodiment, the imaging system is lightweight and supported in such a way as to allow the user to view it conveniently while operating the positioning system. More preferably, the monitor is worn around the user's neck as shown in FIG. 1. Still more preferably, the monitor is contained in a bag or similar device to provide shielding from the sun to improve view ability and reduce glare. For example, the monitor/recording functionality may be supported by a bag 29 as shown in FIG. 1b adapted to be worn around the user's shoulders/neck. The bag 29 preferably has a hook & loop fastened flap 33 and is configured to support a recording device 31 and a monitor 32 (shown in dotted lines).

In the preferred embodiment, the output device 210 comprises a recording device for recording one or more images for evaluation later. Preferably, the recording device is a digital framegrabber. The framegrabber is adapted to convert an analog signal to a digital image and conveniently store the image on a computer-readable medium such as a disk. Images may be stored, for example, in JPEG or a bitmap format which is readily-transmitted over conventional telecommunicative links anywhere in the world without loss of resolution. It has been found that having images in such a readily-transmittable form provides others, who need not be on-site, with the opportunity to analyze the images and determine whether an invasive procedure is required while personnel are on site and in position to perform such a procedure.

In a preferred embodiment, the monitor and framegrabber are integrated into a single unit to provide for a conveniently transportable package. Suitable monitors/framegrabbers are commercially available from, for example, Sony Company (Model No. MVC-FDR3).

Alternatively or additionally, another type of recording device may be used. For example, it may be preferable under certain circumstances to use a video tape recorder. Suitable monitor/tape recorders are commercially available from, for example, Sony Company (Model No. GV-D900).

Rather than having the support system self-contained within the inspection system, it may be preferable to integrate its functionality with other systems such as a cleaning system. Referring to FIG. 10, an alternative embodiment of the invention is shown in which some of the support system 1003 functions are supported by a cleaning system 1002. As mentioned above, in this embodiment, the power supply (not shown) of the truck is used to power the inspection system. This is advantageous as the user is no longer encumbered with heavy batteries and the like. Additionally, the operator control functionality 1008 and monitoring and recording functionality 1020 is also mounted to the truck, thereby lightening the load the user must carry.

3. Positioning System 203

The position system 203 functions to position the imaging device to image the desired area. Since the inspection system of the present invention is intended to inspect hard-to-reach areas or areas which are generally inaccessible to humans, it is preferable for the inspection system to be highly maneuverable. In a preferred embodiment, the positioning system comprises a support 212, more preferably an elongated member, which has the housing of the imaging system mounted on one thereof. With such a configuration, a user can insert the end containing the imaging system into, for example, a pipe, and manipulate it to position the imaging system such that the target area is in its field of view. In a more preferred embodiment, the elongated member is a telescoping boom 14 as shown in FIG. 1.

Preferably, the positioning system comprises an articulated mechanism 213 interposed between the housing of the imaging system and the boom to allow the imaging system to move relative to the boom. This articulated mechanism preferably is a trunnion assembly 28 assembly having an axis perpendicular to the axis of the boom as shown in FIG. 1. A simple trunnion is preferred because it provides for independent movement of the imaging device without incurring the cost, weight and complexity of a traditional pan and tilt mechanism, although such mechanisms are nevertheless within the scope of the invention.

In a preferred embodiment, the imaging system is detachable from the positioning system to allow for its stationary operation. Such a configuration may be preferred, for example, in a surveillance application.

4. Location Recording System 215

The location recording system 215 is an automated position locator, preferably a global position system (GPS) which provides the programmable controller with location data regarding the specific position of the imaging system. Such systems are well known. This information then can be automatically recorded along with image data. One can analogize the location data being recorded along with the image data to a date stamp on a photograph. The use of the location data, however, can be much more versatile and involve different graphical displays and output in combination with the image (see, e.g., the discussion above regarding step (d) of the inspection method).

5. Measurement System 214

Figure 6:
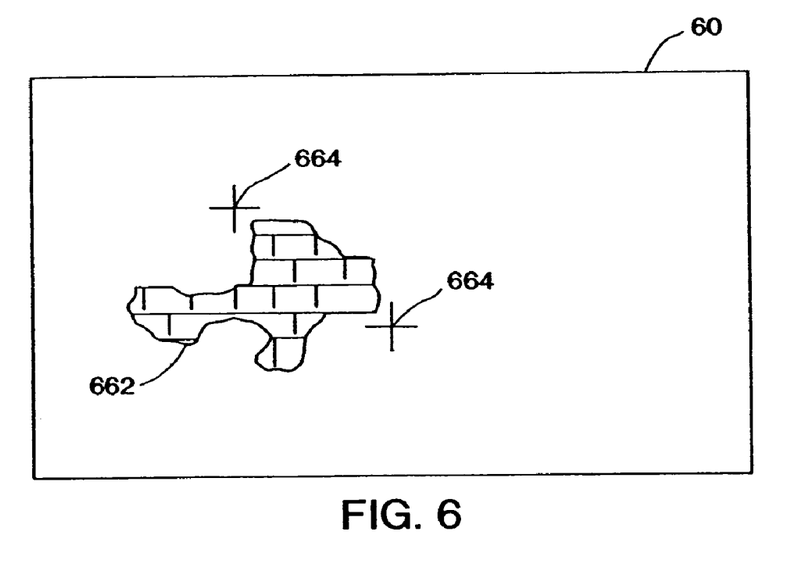
FIG. 6 is a front view of a keypad.
Figure 7:
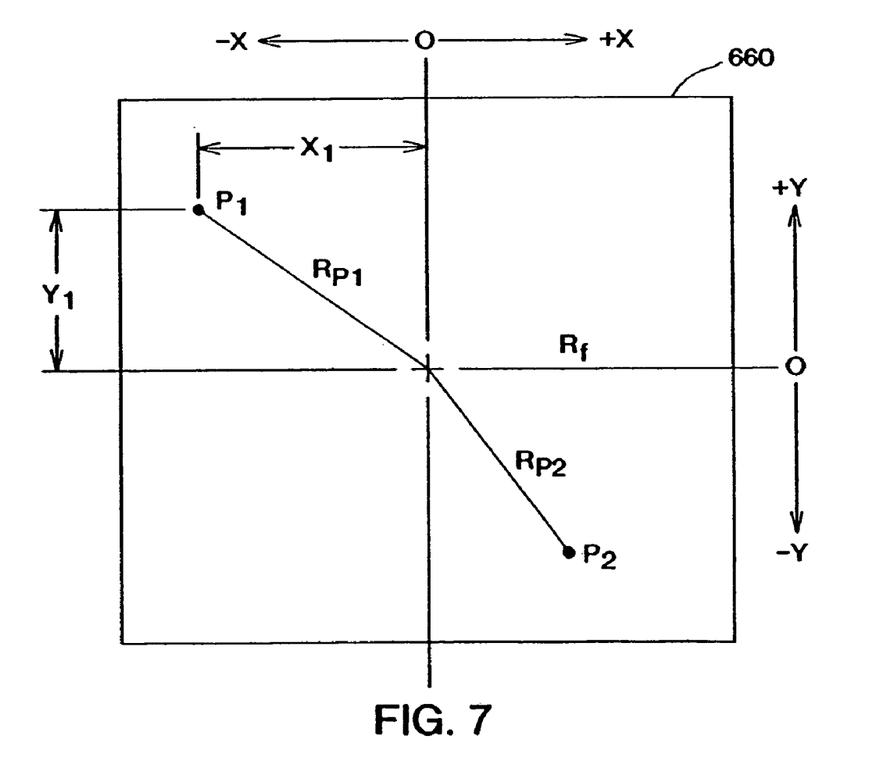
FIG. 7 is a front view of a video screen.

The measuring system functions to provide the user with a measurement of a selected object in the field of view. More specifically, referring now to FIG. 6, a monitor 660 is depicted which displays the video field, including the target object 662 which is to be measured. The monitor is part of the output device 210 as described above. As is known in the art, the monitor 660, or video monitor, comprises a number of pixels. The system includes a video overlay generator 654 (FIG. 3), which generates an information display which overlays the video image. The information display includes measurement cursors 664-664 which are manipulated by the user and are used to mark the target object 662 to be measured, as depicted in FIG. 6. Referring now to FIG. 7, the measurement cursors 764 are controlled by the operator and in the preferred embodiment the operator uses a keypad 770 to control the movements of the cursors. Of course, other means to move and mark the cursor positions are known to those skilled in the art, such as a computer mouse. The keypad 770 preferably is part of the operator's control 211. The keypad 770 includes four cursor positioning keys 772 that move the cursors on the screen in the horizontal and vertical planes. The keypad 770 includes a cursor marking key 774 which, when depressed by the operator, marks the position of the cursor 664 on the screen at one end of the target object 662. The operator then moves the cursor 664 to another point on the screen at the other end of the target object 662. When the second point on the screen has been reached, the cursor marking key 774 is again depressed, and that point is also marked on the screen. In this manner, the operator places marks at the periphery of the target object 662 as it appears on the screen 660. The distance in pixels between the marks is used in the calculation of the size of the target object 662, as explained below in more detail.

Figure 8:
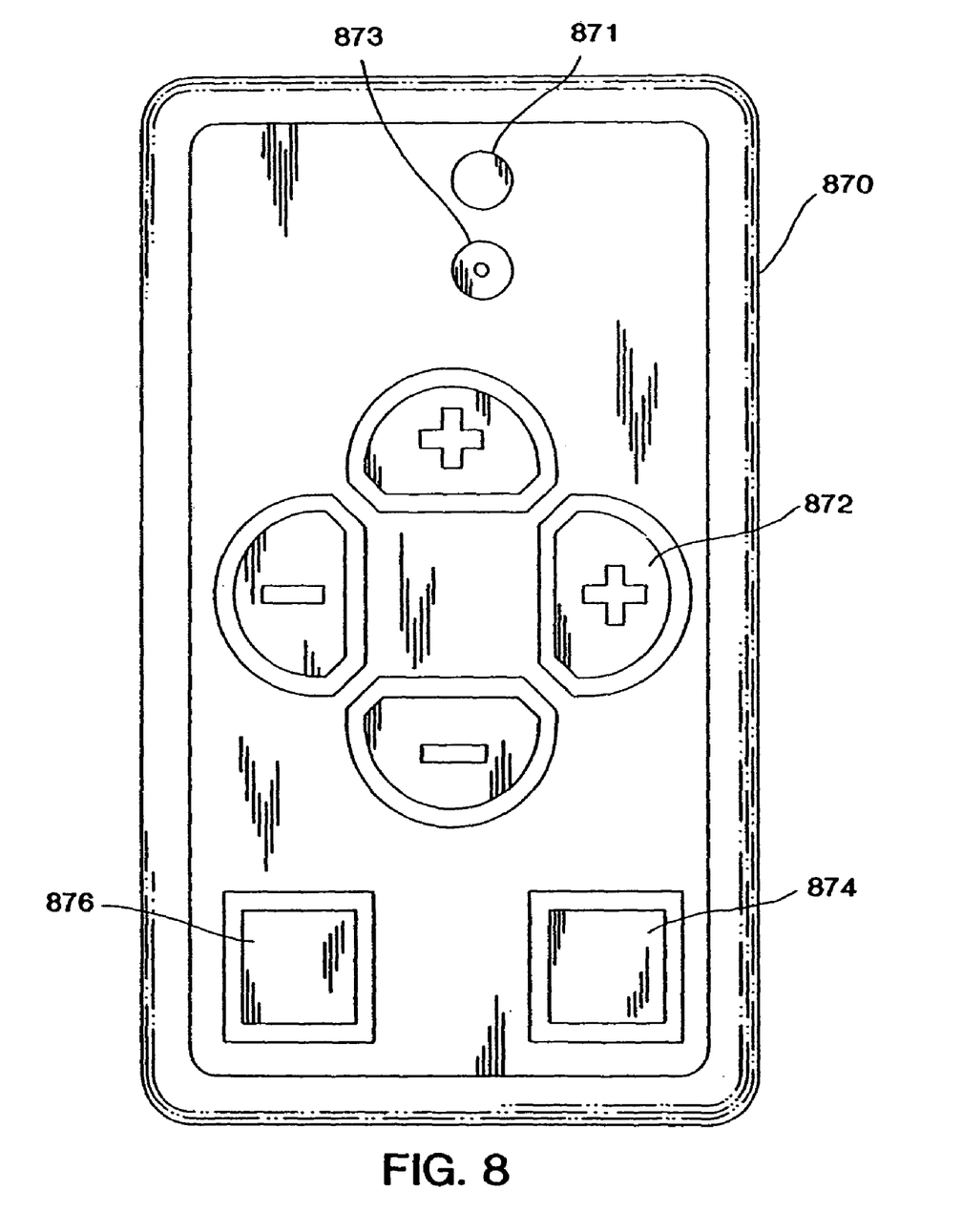
FIG. 8 is a front view of a video screen with a graphical overlay.

In order to determine the size of an object, the first step is to determine the optical distortion correction of a point of the lens/magnification at a given magnification, and preferably for each of calculation, the magnification at M=1× is determined. Referring now to FIG. 8, there is depicted a screen 860 made up of a number of pixels with a graphical representation overlaid to show how the optical distortion correction of a point is used to determine the distance between two points. For simplicity of explanation, the pixels that are depicted have a ratio of 1:1, as opposed to the standard NTSC ratio of 4:3. One skilled in the art would recognize the appropriate mathematical manipulation required to covert between the ratios. The lens/magnification has a known distortion fraction at the flat of square. The optical distortion correction of a point $C_{P1}$ is determined by the formula:

$$C_{P_1} = \frac{1}{1+D_1} = \frac{1}{1+\frac{D(R_{p_1})^2}{R_f^2}}$$

$$C_{P_1} = \frac{1}{\frac{1+D((X_1^2+Y_1^2)^{.5})^2}{R_f^2}}$$

where Rf=Radius to Flat
Rp=Radius to Point
$D_1$=Distortion fraction at Point
D=Distortion fraction at flat of square
$CP_1$=Correction factor for distortion unmapping of $P_1$.

After the optical distortion correction factor is determined for a point, the value of the coordinates at any two particular points can be determined by:

$X_{1_c}$=Distortion Corrected=$C_{P_1}X_1$ $Y_{1_c}$=Distortion Corrected=$C_{P_1}Y_1$ $X_{2_c}$=Distortion Corrected=$C_{P_1}X_2$ $Y_{2_c}$=Distortion Corrected=$C_{P_1}Y_2$ Knowing the distortion corrected values, the distance Pn between points $P_1(X_1Y_1)$ and $P_2(X_2Y_2)$ is determined by $Pn=((X_{1_c}-X^2_c)^2+(Y_{1_c}-Y_{2_c})^2)^{0.5}$ Knowing the value of Pn at magnification M=1, the size of a target object on the video screen after the operator has brought the object into view and focused is determined by:

Object Size=$M*K*Pn$

Where K is a constant

The constant K is determined by using the known characteristics of the lens. The constant K will vary depending upon the type of lens and imager used, but once the characteristics are determined for a particular lens and imager, the number is a constant. The constant K may also contain the conversion math for the measurement system, i.e., inches, centimeter, or millimeters. The calculation of K is determined using the following formula:

$$K = \frac{1}{(\# \text{ of pixels})*L}$$

where L is determined by:

$$L = \frac{\left(\frac{1}{(1-V)}\right)}{2*OD*\text{TAN}\left(\frac{FOV}{2}\right)}$$

where V=the percent distortion across the horizontal axis of lens
OD=Object Distance
FOV=Field of View (across an axis, preferably the horizontal axis)

Figure 9:
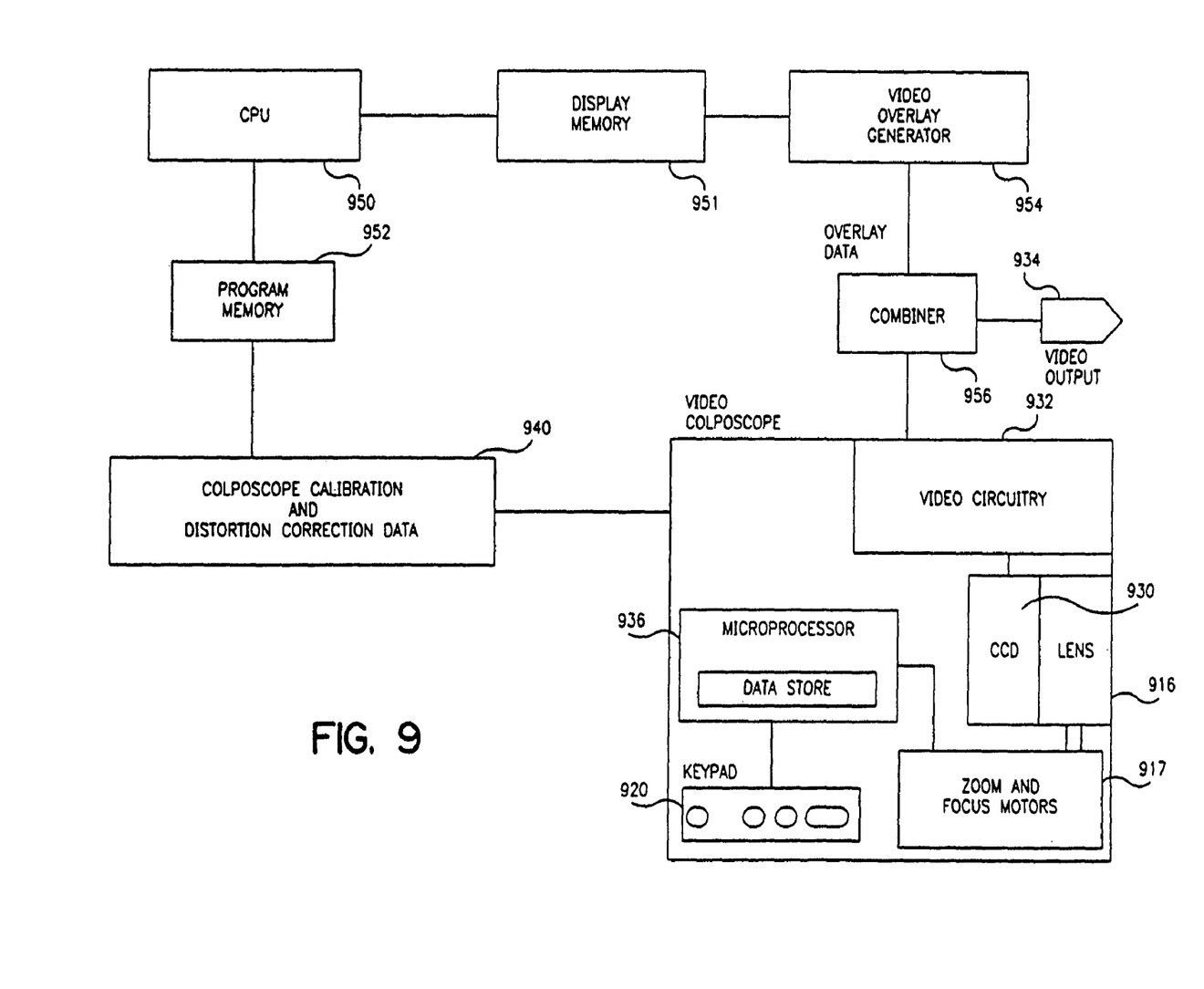
FIG. 9 is a block diagram of the imaging system.

In use, the imaging system is positioned to provide an adequate view of the target area 662. Referring to FIG. 9, the imaging system 910 is automatically calibrated 40 when powered up, which includes the distortion correction data and also includes the focus and magnification motors being zeroed. The target object 662 is brought into the preferred viewing configuration on the screen 660 by the operator using the focus 821 and zoom buttons 822. The exact object distance (OD) is determined by feedback from the focus motor 917 and calculating the deviation from zero. The magnification factor M is determined by the position of the zoom and focus motor 917 servo-feedbacks and is stored in data storage/microprocessor 936. The CCD 930 relays the video information to the video circuitry 932, which then relays the video information to the video output 934 via a combiner 956. The video display information is also stored in display memory 951. The video overlay generator 954 is activated by the operator manipulating the keypad 870 (FIG. 8) by depressing the measurement key 871, which causes the generation of the on-screen cursor 864. The operator manipulates the cursor 664 to mark the periphery of the object 662 using the cursor keys 872 and the marking key 874. After the operator has marked the periphery of the object, the operator depresses the measuring key 876 which causes the overlay data from the combiner 956 to be forwarded to the CPU 950. The size of the object is determined using the calculation algorithms which are stored in program memory 952. The operator returns the imaging system to non-measurement mode by depressing the imaging system key 873.

Of course, in addition to the linear size of an object, the area of an object can also be calculated. For example, the area of a generally square shaped object could be determined by marking the four corners of the object, determining the distance defined by the four corners using the method discussed above, and then applying the appropriate geometrical formula.

While the present invention has been particularly shown and described with reference to the preferred mode as illustrated in the drawing, it will be understood by one skilled in the art that various changes in detail may be effected therein without departing from the spirit and scope of the invention as defined by the claims.

What is claimed is:

1. A method of inspecting a pipe comprising:
  (a) extending an imaging system into a manhole;
  (b) imaging the interior of said manhole at a first magnification level;
  (c) locating a lateral pipe connected to said manhole;
  (d) imaging the interior of said lateral pipe at a second magnification level greater than said first level;
  (e) evaluating the image of step (d) to determine whether said lateral pipe is acceptable or whether an invasive procedure needs to be performed; and
  (f) preforming said invasive procedure on said lateral pipe if needed.

2. The process of claim 1, wherein said invasive procedure comprises conducting a more comprehensive inspection of said area.

3. The process of claim 2, wherein said more comprehensive inspection comprises invading said target area with robotic imaging equipment.

4. The process of claim 1, wherein said invasive procedure comprises cleaning said target area.

5. The process of claim 4, wherein said cleaning involves invading said area with a cleaning tool.

6. The process of claim 5, wherein said cleaning is performed using a mobile vehicle.

7. The process of claim 4, further comprising reiterating steps (a)–(f) until said area is evaluated as acceptable.

8. The process of claim 1, wherein step (d) comprises storing a digital signal corresponding to said image in a database.

9. The process of claim 8, wherein said database comprises data corresponding to the location of the target area.

10. The process of claim 1, wherein step (d) comprises displaying a map indicating the location of said target area.

* * * * *